(12) United States Patent
Bettiol

(10) Patent No.: US 10,631,544 B2
(45) Date of Patent: Apr. 28, 2020

(54) BACTERIAL FORMULATION FOR BIOCONTROL OF PLANT DISEASES AND PROMOTION OF PLANT GROWTH

(75) Inventor: Wagner Bettiol, Campinas (BR)

(73) Assignee: EMPRESA BRASILEIRA DE PESQUISA AGROPECUÁRIA—EMBRAPA, Norte Plano Piloto, Brasilia (BR)

( * ) Notice: Subject to any disclaimer, the term of this patent is extended or adjusted under 35 U.S.C. 154(b) by 0 days.

(21) Appl. No.: 13/881,936

(22) PCT Filed: Oct. 27, 2011

(86) PCT No.: PCT/BR2011/000401
§ 371 (c)(1),
(2), (4) Date: Oct. 7, 2013

(87) PCT Pub. No.: WO2012/055000
PCT Pub. Date: May 3, 2012

(65) Prior Publication Data
US 2014/0026258 A1    Jan. 23, 2014

(30) Foreign Application Priority Data

Oct. 27, 2010    (BR) .................................. 1004530

(51) Int. Cl.
*A01N 63/00*    (2020.01)
*A01N 63/04*    (2006.01)
*A61K 35/74*    (2015.01)

(52) U.S. Cl.
CPC ............. *A01N 63/04* (2013.01); *A01N 63/00* (2013.01); *A61K 35/74* (2013.01)

(58) Field of Classification Search
CPC .................................................... A01N 63/00
See application file for complete search history.

(56) References Cited

PUBLICATIONS

Ganeshan et al., Pseudomonas fluorescens, a potential bacterial antagonist to control plant diseases, Journal of Plant Interactions, 2007, vol. 1, pp. 123-134.*
Coir Institute, Coir Peat accessed on Jan. 12, 2013, http://www.coirinstitute.com/coir_peat.htm.*
Aanen et al., Biological pest control in beetle agriculture, Trends in Microbiology, May 2009, vol. 17, 179-182.*
Sutton et al., Etiology and epidemiology of Pythium root rot in hydroponic crops: Current knowledge and perspectives, Summa Phytopathologica, 2006, vol. 32, pp. 307-321.*

(Continued)

*Primary Examiner* — Rosanne Kosson
(74) *Attorney, Agent, or Firm* — Sughrue Mion, PLLC

(57) ABSTRACT

The present invention relates to bacterial formulation in vegetable fiber materials, which can be employed by incorporation into soils and by treating seeds, as well as in nutrient in hydroponic systems, for the promotion of plant growth and/or the biologic control of diseases. Preferably, the formulation of the present invention employs coconut fiber.
An advantage of the present invention is the possible replacement of turf and other organic or inorganic materials employed in the formulation of inoculants and of agents for the biologic control of bacteria and fungi by coconut fiber.

14 Claims, 4 Drawing Sheets

(56) References Cited

PUBLICATIONS

Smirnov et al., "Antimicrobial and entomopathogenic properties of various strains of Pseudomonas aureofaciens," Prikladnaya Biokhimiya i Mikrobiologiya 35(4):413-416, 1999, English abstract only.*

Chatterton et al., "Timing Pseudomonas chlororaphis applications to control Pythium aphanidermatum, Pythium dissotocum, and root rot in hydroponic peppers," Biological Control 30:360-373, 2003.*

* cited by examiner

BACTERIAL FORMULATION FOR BIOCONTROL OF PLANT DISEASES AND PROMOTION OF PLANT GROWTH

CROSS REFERENCE TO RELATED APPLICATIONS

This is a National Stage of International Application No. PCT/BR2011/000401, filed Oct. 27, 2011 claiming priority from Brazilian Patent Application No. 012100001151, filed Oct. 27, 2010, the contents of all of which are incorporated herein by reference in their entirety.

FIELD OF THE INVENTION

The present invention relates to a bacterial formulation in vegetable fiber materials and can be used by incorporating the formulation into soils and treating seeds, as well as in a nutrient solution in hydroponic systems, for promoting plant growth and/or biological control of diseases. Preferably, the formulation of the present invention uses coconut fiber.

The advantage of the present invention is a possible substitute for turf and other organic or inorganic materials used in formulating inoculants and bacterial and fungal agents for biological control by the action of coconut fiber.

BACKGROUND OF THE INVENTION

The biocontrol agent formulation is a fundamental step for using these microorganisms in agriculture. Among the advantages of the bioagent formulation, one can cite the prolongation of the shelf-life of the microorganisms, the efficacy, growth and survival thereof in the environment, coupled to the compatibility with cultural practices (MARTIN, F. N.; LOPER, J. E. Soilborne plant disease caused by *Pythium* spp.; ecology, epidemiology, and prospects for biological control. Critical Reviews in Plant Sciences, v. 18, n 2, p. 111-181, 1999). Different products may be used in the biological-control agent formulation, which are organic or inorganic, as for instance, talc, turf, kaulinite and vermiculite (NAKKEERAN, S.; DILANTHA, W. G. F.; SIDDIQUI, Z. A. Plant growth promoting rhizobacteria formulations and its scope in commercialization for the management of pests and diseases. In. PGPP: Biocontrol and Biofertilization, Ed. Siddiqui, Z. A. p. 257-296, 2005).

The prior art shows that coconut fiber and the *Pseudomonas* bacterium have already been used separately as a part of the composition in biological control formulations (WO2009135289, US2009274646, JP2008120752, US2002146394, WO200265836, DE29910002, ZA9510628) and biofertilizers (U.S. Pat. No. 7,405,181, NL1005417, GB2252553, FR2722058, CN101624319, CN101497542, CN101468924, CN101284740, CN101054568, RO85118), but none of these documents shows the relationship between the use of coconut fibers and Pseudomona bacterium for biological control of plant diseases, promoting plant growth and, biofertilizing agente and with such efficiency.

Formulations with Gram-positive bacteria, such as those of the genus *Bacillus*, are more frequent on the market, when compared with Gram-negative bacterium formulations, such as those belonging to the genus *Pseudomonas* (BETTIOL, W.; MORANDI, M. A. B.; PINTO, Z. V.; PAULA-JÚNIOR, T. J.; CORRÊA, E. B.; MOURA, A. B.; LUCON, C. M. M.; COSTA, J. C. B.; BEZERRA, J. L. Commercial bioprotectors for controlling plant disease—part I. In. Annual Review of Plant Pathology, Ed. Luz, W. C. p. 111-148, 2009).

Bacteria of the genus *Bacillus* produce endospores, resistant structures that guarantee a long shelf-life for the formulated product. As an example of the longer shelf-life of products formulated with the different groups of bacteria, one can cite the 2-year shelf-life of the Companion® product, formulated with *Bacillus subtilis* GB03, and the 56-day shelf-life of the products Cedomon® and Cerall®, formulated with *Pseudomonas chlororaphis*, at the same temperature.

Bacteria of the genus *Pseudomonas* have a high potential for the development of commercial products, due to the high effectiveness in controlling plant disease of the aerial part and of the root system in different types of crops (KHAN, A.; SUTTON, J. C.; GRODZINSKI, B. Effects of *Pseudomonas chlororaphis* and root rot in peppers grown in small-scale hydroponic troughs. Biocontrol Science and Technology, v. 13, n. 6, p. 615-630, 2003; NAKKEERAN, S., KAVITHA, K., CHANDRASEKAR, G., RENUKADEVI, P., AND FERNANDO, W. G. D. Induction of plant defence compounds by *Pseudomonas chlororaphis* PA23 and *Bacillus subtilis* BSCBE4 in controlling damping-off of hot pepper caused by *Pythium aphanidermatum*. Biocontrol Science Technology, v. 16, p. 403-416, 2006; STOCKWELL, V. O.; STACK, J. P. Using *Pseudomonas* spp. for integrated biological control. Phytopathology, v. 97, p. 244-249, 2007).

Various action mechanisms for biological control of plant disease have been discovered with the study of this bacterium genus (BAKKER, P. A. H., PIETERSE, C. M. J., AND VAN LOON, L. C. Induced systemic resistance by fluorescent *Pseudomonas* spp. Phytopathology, v. 97, p. 239-243, 2007; BLOEMBERG, G. V., AND LUGTENBERG, B. J. J. Molecular basis of plant growth promotion and biocontrol by rhizobacteria. Current Opinion of Plant Biology, v. 4, p. 343-350, 2001; KLOEPPER, J. W.; TUZUN, S.; KUC, J. Proposed definitions related to induced disease resistance. Biocontrol Science Technology, v. 2, p. 349-351, 1992). However, there are few studies regarding the *Pseudomonas* formulation. This fact can be explained due to the sensitivity of this genus to the various conditions and, as a result, and difficult formulation and commercial application (PAULITZ, T. C.; BÉLANGER, R. R. Biological control in greenhouse systems. Annual Review Phytopathology, v. 39, p. 103-133, 2001).

Formulations of species of *Pseudomonas* with substrates based on talc and turf were suggested by Vidhyasekaran and Muthamilan (VIDHYASEKARAN, P.; MUTHAMILAN, M. Development of formulation of *Pseudomonas fluorescens* for control of chickpea wilt. Plant Disease, v. 79, p. 782-785, 1995), Krishnamurthy and Gnanamanickan (KRISHNAMURTHY, K., AND GNANAMANICKAN, S. S. Biological control of rice blast by *Pseudomonas fluorescens* strain Pf714: Evaluation of a marker gene and formulation. Biological control, v. 13, p. 158-165, 1998), Wiyono et al. (WIYONO, S.; SCHULZ, D. F.; WOLF, G. A. Improvement of the formulation and antagonistic activity of *Pseudomonas fluorescens* B5 through selective additives in the pelleting process. Biological Control, v. 46, p. 348-357, 2008), Kloepper e Schroth (KLOEPPER, J. W.; SCHROTH, M. N. Development of a power formulation of rhizobacteria for inoculation of potato seed pieces. Phytopathology, v. 71, p. 590-592, 1981), Nakkeeran et al. (NAKKEERAN, S., KAVITHA, K., CHANDRASEKAR, G., RENUKADEVI, P., AND FERNANDO, W. G. D. Induction of plant defense compounds by *Pseudomonas chlororaphis* PA23 and *Bacillus subtilis* BSCBE4 in controlling damping-off of hot pepper caused by *Pythium aphanidermatum*. Biocontrol Science Technology, v. 16, p. 403-416, 2006), Vidhyasekaran e Muthamilan (VIDHYASEKARAN, P.; MUTHAMILAN, M. Evaluation of a powder formulation of *Pseudomonas fluorescens* Pf1 for control of rice sheath blight. Biocontrol Science Technology, v. 9, p. 67-74, 1999) and Vidhyasekaran et al. (VIDHYASEKARAN, P., SETHURAMAN, K., RAJAPPAN, AND VASUMATHI, K. Power formulations of *Pseudomonas fluorescens* to control pigeon-pea wilt. Biological Control, v. 8, p. 166-171, 1997); with shelf-life ranging from 2 months at 4° C. (KLOEPPER, J. W.; SCHROTH, M. N. Development of a power formulation of rhizobacteria for inoculation of potato seed pieces. Phytopathology, v. 71, p. 590-592, 1981) to 12 months at 5° C. (WIYONO, S.; SCHULZ, D. F.; WOLF, G. A. Improvement of the formulation and antagonistic activity of *Pseudomonas fluorescens* B5 through selective additives in the pelleting process. Biological Control, v. 46, p. 348-357, 2008).

The agroindustrial wastes obtained by processing unripe or ripe coconut have been used in improving fibers as fuel for boilers in the production and carpets and upholstery and in the formulation of substrates for agricultural use. The use of coconut fiber in various industrial segments is an alternative to minimize the environmental impact caused by this solid residue (CEMPRE. Perfil de recicladora de fibras de coco (Profile of coconut fiber recycler) São Paulo, 1998. Reciclagem & Negócio:Fibra-de-coco.35p; ROSA, M. F.; SANTOS, J. S. S.; MONTENEGRO, A. A. T.; ABREU, F. A. P.; ARAÚJO, F. B. S.; NORÕES, E. R. Characterization of the unripe coconut bark powder used as agricultural substrate. Fortaleza: Embrapa Agroindústria Tropical, 2001. 6p. Comunicado Técnico, 5; MOREIRA, M. A., DANTAS, F. M., SANTOS, C. P. D., OLIVEIRA, L. M. D., AND MOURA, L. C. Produção de mudas de pimentão com o use de pó de coco (Production of pimiento by using coconut powder) Rev. Fap., v. 4, p. 19-26, 2008).

*Pseudomonas chlororaphis* 63-28 is one of the best bacterial isolates used for controlling root rot and promoting growth in domestic cultivation of vegetation in Canada (PAULITZ, T. C.; BÉLANGER, R. R. Biological control in greenhouse systems. Annual Review Phytopathology, v. 39, p. 103-133, 2001), being an efficient agent for biological control and promotion of growth in hydroponics (GAGNÉ, S.; DEHBI, L.; LE QUÉRÉ, D.; CAYER, F.; MORIN, J-L.; LEMAY, R.; FOURNIER, N. Increase of greenhouse tomato fruit yields by plant growth-promoting rhizobacteria (PGPR) inoculated into the peat based growing media. Soil Biology Biochnology, v. 25, p. 269-272, 1993; LIU, W.; SUTTON, J. C.; GRODZINSKI, B.; KLOEPPER, J. W.; REDDY, M. S. Biological control of *Pythium* root rot of chrysanthemum in small-scale hydroponic units. Phytoparasitica, v. 35, p. 159-178, 2007; OWEN-GOING, T. N.; SUTTON, J. C; GRODZINSKI. Relationship of *Pythium* isolates and sweet pepper plants in single-plant hydroponic units. Canadian Journal of Plant Pathology, v. 25, p. 155-167, 2003). Besides the efficient competition for space and nutrients with cross-link pathogens, the bacterial isolate produces antibiotics, induces resistance to the plants and produces plant growth hormones (PAULITZ, T. C.; BÉLANGER, R. R. Biological control in greenhouse systems. Annual Review Phytopathology, v. 39, p. 103-133, 2001; ZHENG, J., SUTTON, J. C., AND YU, H I. Interactions among *Pythium aphanidermatum* roots, root mucilage, and microbial agents in hydroponic cucumbers. Canadian Journal of Plant Pathology, v. 22, p. 368-379, 2000). Due to the effectiveness of *Pseudomonas chlororaphis* 63-28 as a biological control agent, the project SYNERGIE was implemented in Canada, where one of the purposes was to formulate *Pseudomonas chlororaphis* 63-28 in turf for use in protected cultures, with shelf-life from six months to one year. The researchers found higher survival of the isolate 63-28 in turf with the moisture of 100-150% (v/v) and lower survival in turf with the moisture of 45% and 25%. However, even in the best units the bacterial population dropped to levels lower than $10^6$ ufc/g after 1 to months (PAULITZ, T. C.; BÉLANGER, R. R. Biological control in greenhouse systems. Annual Review Phytopathology, v. 39, p. 103-133, 2001).

On the international market there the bioproducts Cedomon® e Cerall® (Bioagri, Sweden) are available for the treatment of seeds of oat, barley and wheat, formulated with *Pseudomonas chlororaphis*. The shelf-life of the bioproducts is of 56 days when they are stored at 4° C.-8° C. and of 21 days at room temperature (LANTMANNEN BIOAGRI: http://www.bioagri.se/pseudomonas_eng.html, access on Sep. 25, 2009). The formulation of the present invention demonstrates that *Pseudomonas chlororaphis* 63-28 has shelf-life of 224 days at 3±1° C. when formulated on coconut fiber, demonstrating that the coconut fiber is very useful for the formulation with this bacterium.

Barriers to the commercial use of *Pseudomonas* spp. Include the lack of information about the formulation technology that would optimize the cost of mass production and the application of biocontrol agents (WIYONO, S.; SCHULZ, D. F.; WOLF, G. A. Improvement of the formulation and antagonistic activity of *Pseudomonas fluorescens* B5 through selective additives in the pelleting process. Biological Control, v. 46, p. 348-357, 2008). The results achieved in developing the formulation with coconut fiber indicate the feasibility of its use for *Pseudomonas*, formulations due to its high shelf-life.

One of the applications of the present invention lies in the use of the formulation in plant development, mainly in hydroponic crops, with a view to promote plant growth.

Ever since the hydroponic cultivation began to be employed on a commercial scale in the year 1940, it has been growing all ove the world (FURLANI, P. R.; BOLONHEZI, D.; SILVEIRA, L. C. P.; FAQUIN, V. Nutrição mineral de hortaliças, preparo e manejo de soluções nutritivas (=Mineral nutrition of vegetables). Informe Agropecuário, v. 20, n. 200/201, p. 90-98, 1999; FURLANI, P. R. Simpósio IV—*Pythium* em sistemas hidropônicos—danos e perspectivas para o controle: Principais sistemas hidropônicos em operação no Brasil. Summa Phytopathologica, v. 34, p. 146-147, 2008; STANGHELLINI, M. E.; RASMUSSEN, S. L. Hydroponics a solution for zoosporic pathogens. Plant Disease, v. 78, n. 12, p. 1129-1138, 1994). The increase in hydroponic cultivation is due to the advantages provided in the vegetable production by this system, such as the standardization of the production, anticipation of the crop cycle, reduction in the use of water, efficiency in the use of fertilizers and larger production per area (FURLANI, P. R.; BOLONHEZI, D.; SILVEIRA, L. C. P.; FAQUIN, V. Nutrição mineral de hortaliças, preparo e manejo de soluções nutritivas. Informe Agropecuário, v. 20, n. 200/201, p. 90-98, 1999). These advantages are, to a great extent, responsible for the use of nutrient solution that provides the necessary nutrients, keeping the composition close to the roots and maintaining the adequate concentration of nutrients, besides the control of the pH of solution, keeping the latter at levels suitable for the absorption of nutrients (FAQUIN, V.; FURLANI, P. R. 1999. Cultivo de hortaliças de folhas em hidroponia em ambiente protegido. *Informe Agropecuário* 20: 99-104; FERNANDES, A. A.; MARTINEZ, H. E. P.; PEREIRA, P. R. G.; FONSECA, M. C. M. Produtividade, acúmulo de nitrato e estado nutricional de cultivares de alface, em hidroponia, em função de fontes de nutrientes. Horticultura Brasileira, v. 20, n. 2, p. 195-200, 2002; MEDEIROS, C. A. B.; ZIEMER, A. H.; DANIELS, J.; PEREIRA, A. S. Produção de sementes pré-básicas de batata em sistemas Hidropônicos. Horticultura Brasileira, Brasília, v. 20, n. 1, p. 110-114, 2002).

Presently, the hydroponic production is concentrated on vegetables and flowers, being employed in producing lettuce, eruca (*Eruca sativa*), water-cress, wild chicory, cole, chives, celery, tomato, cucumber, pimento, strawberry, tubercles and flowers (FAQUIN, V.; FURLANI, P. R. 1999. Cultivo de hortaliças de folhas em hidroponia em ambiente protegido. Informe Agropecuário 20: 99-104; Chatterton, S.; Sutton, J. C. e Boland, G. J. 2004. Timing *Pseudomonas chlororaphis* applications to control *Pythium aphanidermatum*, *Pythium dissotocum*, and root rot in hydroponic peppers. Biological Control 30: 360-373; PAULITZ, T. C.; ZHOU, T. & RANKIN, L. Selection of rhizosphere bacteria for biological control of *Pythium aphanidermatum* on hydroponically-grown cucumber. Biological Control, v. 2, p. 226-237. 1992.; MEDEIROS, C. A. B.; ZIEMER, A. H.; DANIELS, J.; PEREIRA, A. S. Produção de sementes pré-básicas de batata em sistemas hidropônicos. Horticultura Brasileira, Brasília, v. 20, n. 1, p. 110-114, 2002). In Brazil, the main crop produced in hydroponics is lettuce, this production being located chiefly close to metropolitan regions.

Since the creation of hydroponic systems, these have been modified for better adaptation to environmental, social and economical conditions of each region, with a view to improve the quality and increase the productivity of crops (ANDRIOLO, J. L.; LUZ, G. L.; GIRALDI, C.; GODOI, R. S.; BARROS, G. T. Cultivo hidropônico da alface empregando substratos: uma alternativa a NFT? Horticultura Brasileira, v. 22, n. 4, p. 794-798, 2004). The main hydroponic systems employed are the nutrient film technique (NFT), deep film technique (DFT) or floating, cultivation in substrate and aeropony. The NFT system is the most widely employed technique in Brazil for cultivating leaf vegetables, wherein the nutrient solution is pumped into the channels and pours by gravity, forming a thin solution film that irrigates the roots. The DFT technique is employed by using a deep film of nutrient solution (5 to 20 cm), the plants being placed on a flat table where the solution circulates by pumping and gravity. The cultivation on substrate is used chiefly for large-size crops like cucumber, pimiento and tomato, wherein the nutrient solution circulates through the substrate, which is generally inert, like sand, expanded clay, vermiculite, rock wool, turf and coconut fiber, returning to the nutrient solution tank. In aeropony cultivation the plant roots remain suspended, receiving water and nutrients by means of sprays (FAQUIN, V.; FURLANI, P. R. 1999. Cultivo de hortaliças de folhas em hidroponia em ambiente protegido. Informe Agropecuário 20:99-104).

Root rot caused by species of *Pythium* is a serious problem for hydroponic cultivation all over the world. Resistant cultivars are not available for the producer, and there are no registered fungicides for use in hydroponics. The main measure for controlling the disease is to prevent the pathogen from getting into the system. Once the disease has installed itself, the suppression thereof may be carried out by adding biological control agents to the nutrient solution. Besides controlling the disease, the introduction of beneficial microorganisms can promote plant growth, increasing the agriculturist's income. The present invention At present, the main products studied and used for the formulation of bacteria of the genus *Pseudomonas* are talc, turf, saw-dust, diatomaceous earth, bentonite, cotton meal, vermiculite and wheat bran. One of the advantages of the present technology lies in using an organic substrate, which is abundant as a waste in Brazil, does not contaminate the soil and does not degrade the environment.

SUMMARY OF THE INVENTION

The present invention relates to a bacterial formulation for incorporation into soils and treatment of seeds, as well as into nutrient solution for hydroponic systems, with a view to promote plant growth and/or biological control of disease.

One of the embodiments of the invention is a formulation characterized by comprising:
(a) Microorganism cells;
(b) Vegetable fiber material;
(c) Water in sufficient amount to keep the microorganism cells feasible;
(d) Optionally, nutrient additives or growth factors selected from the group consisting of sugars, amino acids, proteins, salts and the like, or mixture thereof;
(e) Optionally, adjuvants selected from osmotic regulating agents, buffering agents or pH adjustment agents.

A second embodiment of the invention relates to the use of the formulation characterized in that said formulation is applied to the seeds of any propagating material intended for plantation.

A third embodiment of the invention relates to the use of the formulation characterized in that said formulation is applied in hydroponic cultures.

A fourth embodiment of the invention relates to a method characterized by applying the formulation in an amount sufficient to control a biological pest.

A fifth embodiment of the invention relates to a method characterized by applying the formulation in an amount sufficient o enable the development of hydroponic plants.

A sixth embodiment of the invention relates to a plant propagating material characterized in that the plants are treated with the formulation.

DETAILED DESCRIPTION OF THE INVENTION

Figure 1:
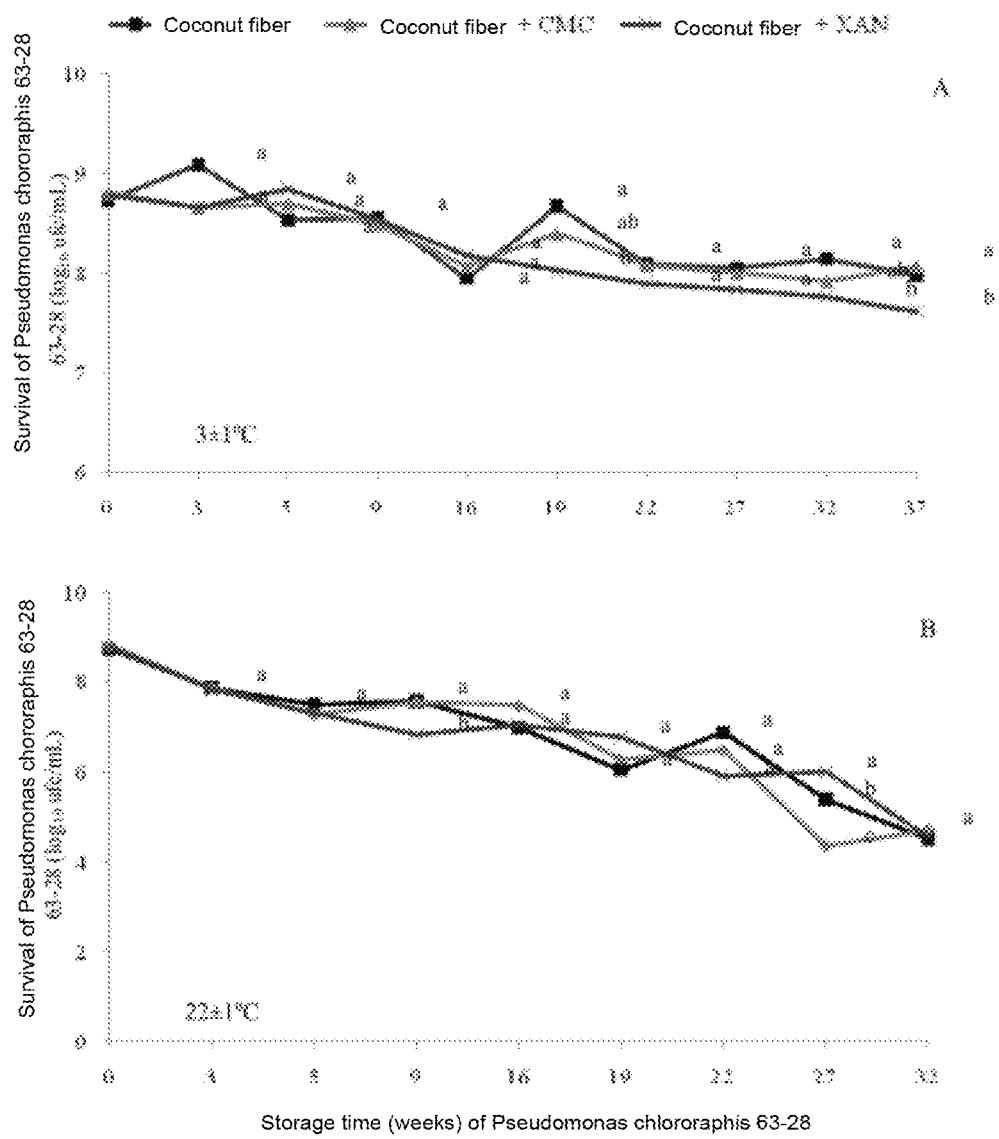
FIG. 1 shows graphs illustrating the survival (shelf-life) of *Pseudomonas chlororaphis* 63-28 in coconut fiber, with or without addition of carboxymethylcellulose (CMC) or xanthan gum (XAN) at temperatures of $3\pm1°$ C. (A) and $22\pm1°$ C. (B).

The present invention relates to a bacterial formulation in vegetable fiber materials and may be used by incorporating the formulation into soils and in treating seeds, as well as in nutrient solutions in hydroponic systems, to promote plant growth and/or biological control of diseases.

The formulation of the present invention is characterized by comprising:

(a) microorganism cells;
(b) vegetable fiber material;
(c) water in an amount sufficient to keep the microorganism cells feasible;
(d) optionally, nutrient additives or growth factors;
(e) optionally, adjuvants selected from osmotic regulating agents, buffering agents, pH adjusting agents.

The term "microorganism" refers to microscopic organisms such as bacteria, virus, fungi and protozoa. Preferably, the present invention has, as microorganisms, the organisms chose from the group of bacteria. "Bacteria" refer to prokaryotic organisms, with the exception of cyanophyciae. The invention has use on various species of bacteria, which include, but are not limited to the group of Actinobacteria, Aquificae, Bacteroidetes/group Chlorobi, Chlamydiae/group Verrucomicrobia, Chloroflexi, Chrisiogenetes, Cyanobacteria, Gloeobacteria, Nostocales, Oscillatoriales, Pleurocapsales, Prochlorales, Stigonematales, Deferribacteres, Deinococcus-Thermus, Dictyoglomi, Fibrobacteres/group Acidobacteria, Firmicutes, Fusobacteria, Gemmatimonadetes, Nitrospirae, Planctomycetes, Proteobacteriz, Spirochaetes, Thermodesulfobacteria, Thermotogae. Preferably, the invention makes use of bacteria selected from the group of plant-growth promoting rhizobacteria, including *Pseudomonas* spp. *Herbaspirillum* spp., *Azospirillum* spp., *Gluconacetobacter* spp., *Burkholderia* spp., and *Bacillus* spp. More preferably, the invention relates to *Pseudomonas*.

The microorganism cells used in the present invention are defined as being colony forming units. Preferably, for the present invention one has used from $1\times10^7$ to $1\times10^{11}$ colony forming units (cfu)/mL.

As used herein, the expression "vegetable material" means each and every material from vegetables such as barks/husks and other fibrous components from seeds and fruits, plant stems. Preferably, for the present invention one has used coconut fibers. The coconut fiber of the present invention can be used as follows: ground in different grain sizes, associated with additives for acidity correction electric conductivity. The amount of coconut fibers used will depend on the grain size thereof, and may range from 1 mm to 10 mm. This grain size will depend on the use of the formulation. For hydroponics, seed treatment, spraying and irrigation, it will be as small as possible (<2 mm). On the other hand, for mixture with substrate or soil, it may be from 1 to 10 mm. Preferably, for the present invention the coconut fiber has been sieved in 2-mm opening sieve and used in the ratio 10:1 (10 g of coconut fiber: 1 ml of bacterium cell suspension.

The present invention is characterized in that the nutrient additives or growth factors are selected from the group consisting of sugars, amino acids, proteins, salts and the like, or mixture thereof.

The present invention further works with adjuvants selected from osmotic regulating agents, buffering agents or pH adjusting agents. Preferably, the present invention uses, as adjuvants, carboxymethylcellulose, gum Arabic, sodium alginate and the like. Preferably, the invention uses calcium carbonate ($CaCO_3$) as a pH adjusting agent to neutralize it in the formulation.

The formulation of the present invention can be used in the biological control of diseases and pests. The pests on which the formulation act may be, but are not limited to, pests of the group containing caterpillars, cankerworms, acaridae, clothes moths, worms, fungal insects, beetles, cochineal insect, white flies, grass-hoppers, flea-insects, cochineal insect, centipedes, plant lice, spiders, ants, and insect larvae. The diseases on which the formulation acts may be caused by fungi, bacteria, zoospore-producing pathogens, pathogens carried into the soil, root pathogens and pathogens of the aerial part of plants. The control of disease of the aerial part of plants is made by means of the resistance inducing mechanism. Particularly, the formulation of the present invention acts on organisms of the kingdom Stramenopilae of the phylum Oomicota of the family Pythiaceae of the genus *Pythium*, and zoospera-producing pathogens.

The formulation of the invention can be applied to seeds and any propagating material intended for plantation. The formulation of the invention may be suspended in water or dispersible, powder, granules or in the form of a seed coating powder.

The formulation of the invention can be applied in hydroponic cultures, seedling producing substrates, substrate for plant growth, soils, nutrient solutions and irrigation water. In nutrient solution and irrigation water, the formulation can be applied directly in tanks. On the other hand, in substrates and soils, it may be mixed before the seeding/planting and afterward via irrigation water.

The invention also describes a method characterized in that one applies the formulation of the invention in an amount effective to control a biological past. The expression "effective amount" may be defined as being the amount necessary to kill or reduce a determined crop pest, or the amount necessary to enable the development of plants. The amount of formulation will depended on the type of pest and crop. For the present invention, one used, as a biological model, the pathosystem lettuce×*Pythium aphanidermatum*. Preferably, for the present invention the final concentration employed was of $10^7$ ufc/mL of nutrient solution.

The formulation of the invention can be applied to seeds, seedlings and any propagating material intended for plantation. The propagating materials of the present invention may be, but are not limited to seedlings, seeds, stalk, bubbles, branches, stock for grafting, stem and all the plant parts liable to be propagated.

The formulation of the invention can further be applied to cultivating substrate and in the nutrient solution.

The invention also describes a method characterized in that one applies the formulation in an amount effective for enabling the development of hydroponic plants, as well as a seedling producing substrate, plant growth substrate and soils. The amount of formulation to enable the development of a plant will depend on the type of crop. For the present invention, one has studied the cultivation of lettuce. The formulation was applied in the nutrient solution, by adding suspensions in the final concentration of $10^7$ ufc/mL of nutrient solution. The formulation for use in hydroponic crops should have adequate grain size (smaller than 2 mm), so that the system will not be clogged. Formulations for use in hydroponic crops that use organic substrate do not have restrictions as to the grain size.

The formulation of the present invention can be used in the form of water suspension or dispersible, in granules, or in the form of a powder for coating seeds and other propagation organs.

EXAMPLES

The present invention is further defined in the following examples. One should understand that, although these examples indicate part of the invention, they are given with a view to illustrate the invention, without being limitative of the scope of the present inventions.

Example 1—Obtainment of the Bacteria

The bacterial isolates sued in the present invention were *Pseudomonas aureofaciens*, strain Tx-1, and *Pseudomonas chlororaphis*, strain 63-28. Both isolates belong to the crop collection of the Guelph University in Canada and were obtained from the company Eco Soils Systems, Inc., San Diego, Canada.

Example 2—Multiplication of the Bacteria

*Pseudomonas* spp. Isolates were cultured in a liquid medium "Tryptic Soy Broth" (TSB—3-10 g/liters of water) per 48 hours in an agitator at 150 rpm at the temperature of 22±1° C. After 48 h, the bacterial suspension was centrifuged at 2000 g for 15 min, the cells being re-suspended and washed by centrifugation at 2000 g for 10 min in buffer $MgSO_4$ 0.1 M.

Example 3—Application of the Bacterial Cells in Coconut Fiber

For evaluation of the shelf-life of *Pseudomonas* spp., in coconut fiber, it was necessary to sieve the fiber. For this purpose, it was ground and sieved with a 425 μm opening sieve, and to neutralize the pH (7) with $CaCO_3$.
In polypropylene sacks having openings for oxygen exchange, one has added the volume of 90 mL of ground and sieved coconut fiber, previously sterilized, the sterilization being carried out by autoclaving for three alternating days at 120° C. the bacterial suspensions at a concentration of 5×109 colony forming units (ufc)/mL were added to the coconut fiber, so that the coconut fiber moisture could be adjusted to 75-80%. The polypropylene sacks containing the coconut fiber with the bacterial suspensions were added at 3±1° C. and 22±1° C., so that the temperature of 3±1° C. could provide longer shelf-life.
Weekly or monthly evaluations were carried out to assess the bacterial population by plating in a TSB medium plus agar.

Example 4—Evaluation of the Shelf-Life of *Pseudomonas chlororaphis* 63-28 and *Pseudomonas aureofaciens* TX-1 in Coconut Fiber with Different Units In order to evaluate the shelf-life of *P. chlororaphis* 63-28 and *P. aureofaciens* TX-1 in coconut fiber (Optimum Hydroponix, Canada), one sieved the fiber with 425-μm-opening and neutralized the pH with CaCO3. The volume of 90 mL of coconut fiber was added in polypropylene sacks having openings for oxygen exchange. The sterilization of the substrate was carried out by autoclaving for 3 alternating days at 120° C. After the autoclaving, the bacterial suspensions were added to the coconut fiber. The moistures coconut fibers were adjusted to 25%, 45% and 75%. The polypropylene sacks containing the coconut fiber with the bacterial suspensions were packed at 3±1° C. and 22±1° C. for 120 days. Monthly evaluations were carried out to assess the bacterial population by plating in TSB medium plus agar, and the moisture of the substrates.

Example 5—Evaluation of the Shelf-Life of *Pseudomonas chlororaphis* 63-28 in Coconut Fiber, Talc, and Turf Longer shelf-life of *P. chlororaphis* 63-28 in coconut fiber, either with or without addition of the additives carboxymethylcellulose or xanthan gum, was verified at 3±1° C., when compared with the shelf-life of the formulations stored at 22±1° C. (FIG. 1).

Statistic differences were found in the $19^{th}$, 32th, and $37^{th}$ storage weeks, the survival of the bacterium being higher in coconut fiber without additives at 3±1° C. (FIG. 1A). The addition of carboximethylcellulose did not increase the survival of the bacteria, and the addition of xanthan gum had a negative effect on the survival of *P. chlororaphis* 63-28 at 3±1° C. (FIG. 1A).

When stored at 22±1° C., the bacterial population dropped by one log ufc $mL^{-1}$ unit of substrate after three weeks. No difference was found with regard to the additives to the formulation, keeping the same log ufc $mL^{-1}$ unit in the coconut fiber formulations with or without additives until five storage weeks (FIG. 1B). After 9-week storage at 22±1° C., the smaller bacterial population was found in the coconut fiber with addition of xanthan gum, and no statistical differences were found between the coconut fiber with or without carboxymethylcellulose (FIG. 1B). Statistic differences were also found after 72-week storage, and a larger bacterial population in coconut fiber with xanthan gum was found, followed by coconut fiber without additives, and with greater survival in coconut fibers with addition of carboxymethylcellulose (FIG. 1B).

The bacterial formulations in turf and talc did not provide the maintenance of the survival of the bacterium in large populations, and they dropped by three log ufc $mL^{-1}$ units after application thereof to substrates (data not shown).

Figure 2:
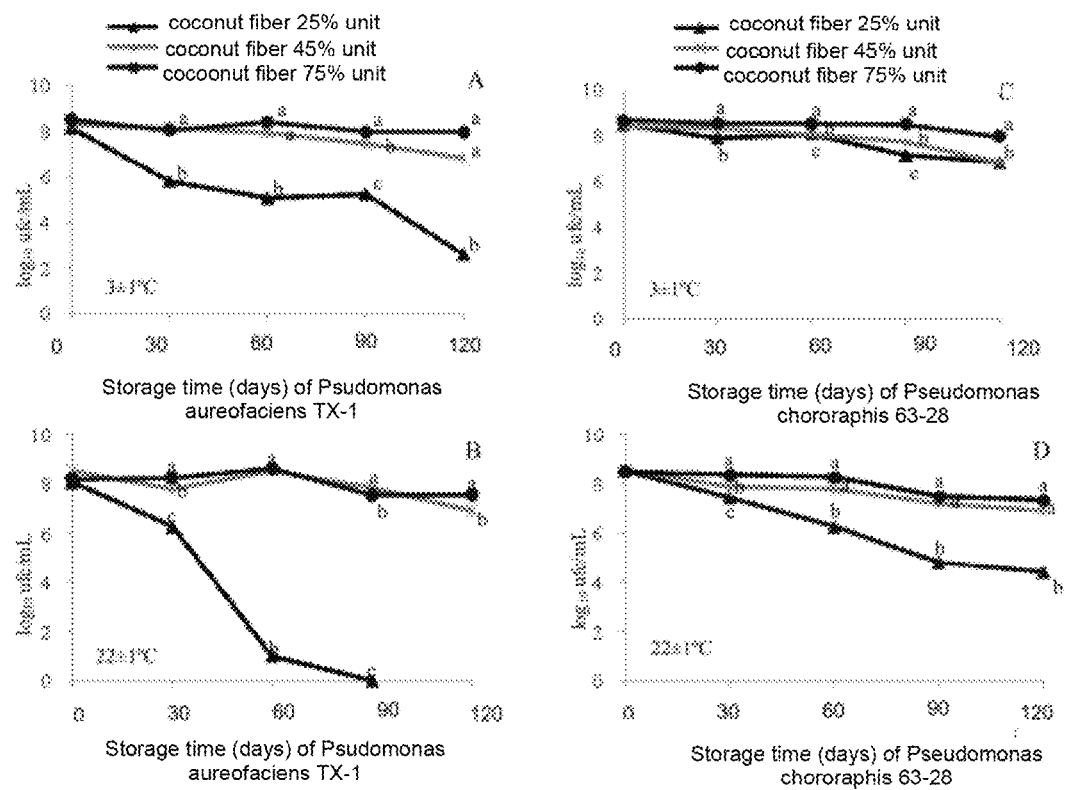
FIG. 2 shows graphs illustrating the survival (shelf-life) of *Pseudomonas aureofaciens* TX-1 (A-B) and *Pseudomonas chlororaphis* 63-28 (C-D) and in coconut fiber with different moistures at temperatures of $3\pm1°$ C. and $22\pm1°$ C.

Example 6—Evaluation of the Shelf-Life of *Pseudomonas chlororaphis* 63-28 and *Pseudomonas aureofaciens* TX-1 in Coconut Fiber with Different Moistures The temperature of 3±1° C., FIG. 2) was more efficient in keeping the shelf-life of *Pseudomonas* spp., when compared with the temperature of 22±1° C. (FIG. 2). The *Pseudomonas* spp formulation in coconut fiber with moisture of 75% provided greater bacterial survival when compared with 45% or 25% moisture (FIG. 2). The moisture of 25% caused a greater reduction in the bacterial population along the time, regardless of the bacterial species employed (FIG. 2).

The population of *P. aureofaciens* TX-1 at 3±1° C. had a similar behaviour in coconut fiber with moistures of 45% and 75% until 60 days' storage. On the $90^{th}$ day of storage, the bacterial population was higher in the substrate with 75% moisture and did not differ on the $120^{th}$ day of storage. Coconut fiber with 25% moisture exhibited the lowest values of bacterial population ion all the periods evaluated (FIG. 2A).

When stored at 22±1° C., the population of *P. aureofaciens* TX-1 was higher in coconut fiber with 75% moisture on the $30^{th}$ day of storage, followed by coconut fiber with 45% and 25% moisture, respectively (FIG. 2B). On the $60^{th}$ day of storage no differences were found between the moistures 75% and 45%, the moisture 25% providing the lowest survival. On the $90^{th}$ and $140^{th}$ days of storage, the coconut fiber with 75% moisture provided better survival of

*P. aureofaciens* TX-1, when compared with the moisture of 45%. It was not possible to recover the bacterial cells in the culture medium of the coconut fiber with 25% moisture on the $90^{th}$ and $140^{th}$ days of storage (FIG. 2B).

The *P. chlororaphis* 63-28 formulation ion coconut fiber with moisture of 75% at a temperature of 3±1° C. remained at the same log ufc mL$^{-1}$ unit of substrate during the 140 days of storage (FIG. 2C). On the $30^{th}$ day, no statistic differences were found in the bacterial population between the moistures of 75% and 45%. However, the moisture of 25% exhibited the lowest value of log ufc (FIG. 2C). During the 60 and 90 days of storage, the bacterial population was higher at moisture 75%, followed by 45% and 25%, respectively. On the $120^{th}$ day, one found greater bacterial population in the coconut fiber with 75%, and no differences were found at 45% and 25% at a temperature of 3±1° C. (FIG. 2C).

The storage of *P. chlororaphis* 63-28 at 22±1° C. caused reduction of one log ufc mL$^{-1}$ unit of substrate in the bacterial population at moisture of 75% on the $90^{th}$ day of storage (FIG. 2D). On the $30^{th}$ day, the population of *P. chlororaphis* 63-28 exhibited the highest values of log ufc when the moisture of 75%, followed by 45% and 25%, respectively (FIG. 2D). During the 60 to 120 days of storage, the bacterial population was similar in the coconut fiber with 75% or 45% of moisture, with the same values of log ufc in the substrate with 25% moisture (FIG. 2D).

Figure 3:
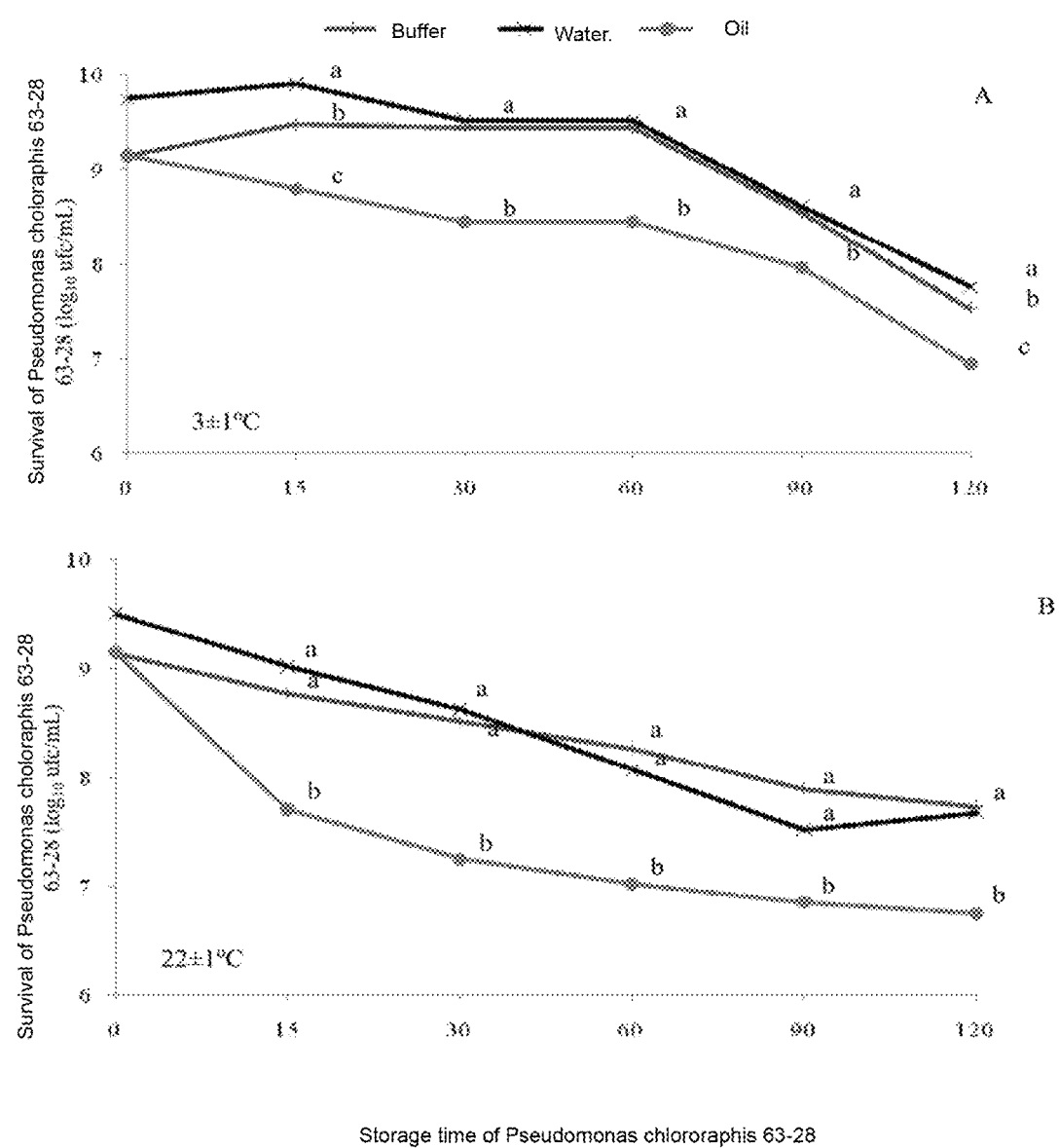
FIG. 3 shows graphs illustrating the survival of *Pseudomonas chlororaphis* 63-28 in water, canola oil and buffer MgSO4 0.1 M at temperatures of $3\pm1°$ C. (A) and $22\pm1°$ C. (B).

Example 7—Evaluation of the Shelf-Life of *Pseudomonas chlororaphis* 63-28 in Water, Canola Oil and Magnesium Sulphate Buffer The temperature of 3±1° C. provided better survival of *P. chlororaphis* 63-28 than the temperature of 22±1° C., regardless of the suspension employed for preserving the bacterium (FIG. 3). With regard to the suspensions employed, the use of water and buffer provided better bacterial survival when compared with the canola oil (FIG. 3). The survival of *P. chlororaphis* 63-28 at the temperature of 3±1° C. was higher in water after 15 and 120 days' storage, followed by buffer and canola oil, respectively (FIG. 3A). During 30, 60 and 90 days' storage, no statistic differences were found between water and buffer. However, canola oil exhibited the lowest values of log ufc when its survival was considered (FIG. 3A). Statistic differences were not found with regard to the bacterial population in water and buffer throughout the experiment at 22±1° C. (FIG. 3B). However, the canola-oil suspensions exhibited the lowest values of ufc in all the periods evaluated (FIG. 3B).

Example 8—Promotion of the Growth of Hydroponic Lettuce by *Pseudomonas chlororaphis* 63-28

Figure 4:
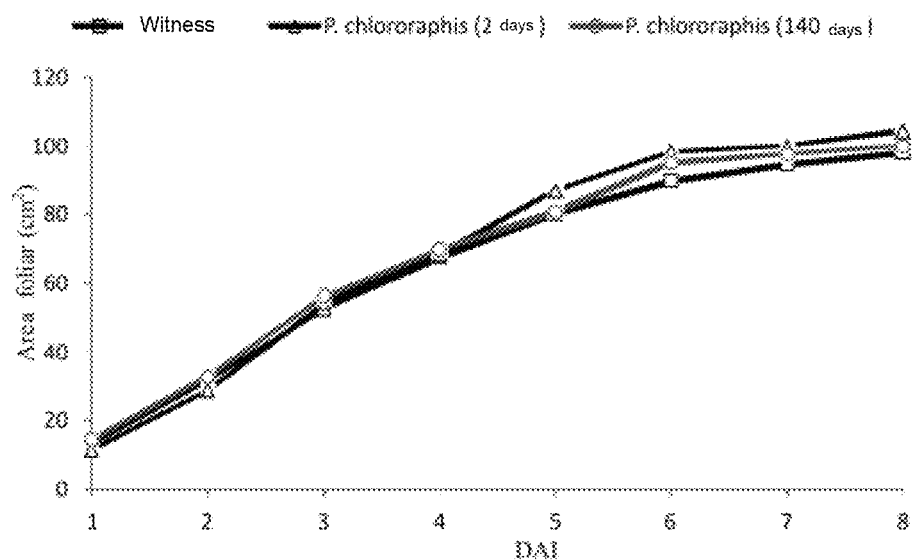
FIG. 4 is a graph showing foliar growth of a young leaf of hydroponic lettuce plant after infestation or without infestation of the nutrient solution with *Pseudomonas chlororaphis* 63-28 cells, multiplied by two days, or *Pseudomonas chlororaphis* 63-28, formulated in coconut fiber and stored for 140 days.

From the fifth days after infestation of the nutrient solution with bacterial suspensions, one found greater foliar growth of the plants in the treatments with infestation of the bacterial suspensions (FIG. 4).

Figure 5:
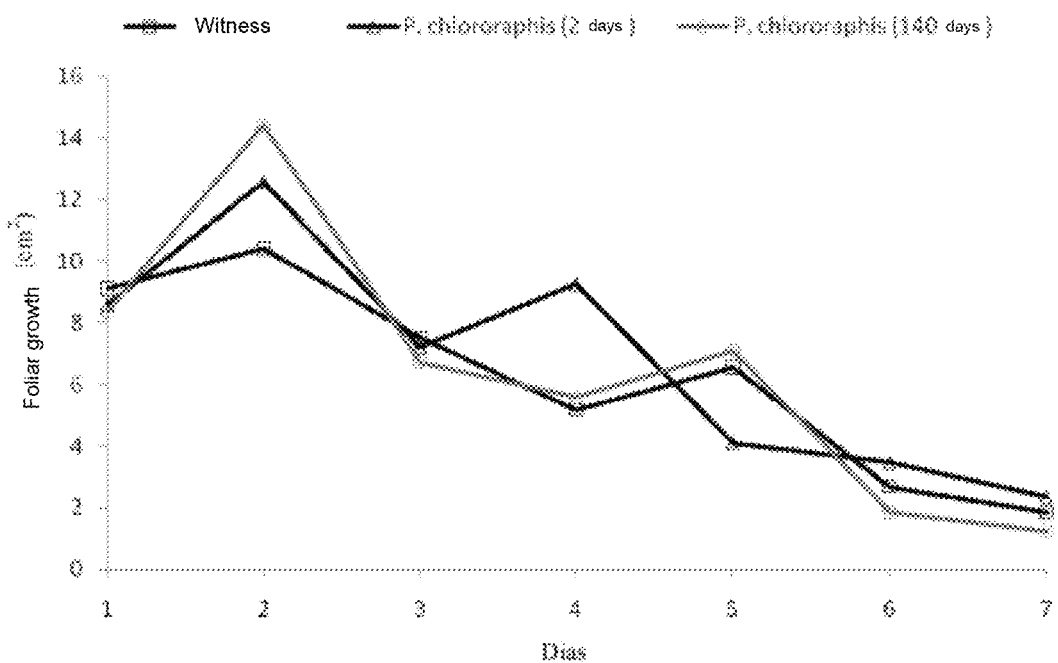
FIG. 5 is a graph showing the foliar growth rate of hydroponic lettuce plants after infestation or without infestation of the nutrient solution with *Pseudomonas chlororaphis* 63-28 (2 days) or *Pseudomonas chlororaphis* 63-28 (140 days).

The date in FIG. 5 show higher foliar growth rate in the lettuce plants infested with bacterial isolates. Folia growth picks were found on the $2^{nd}$ and $5^{th}$ days after infestation of the nutrient solution with *P. chlororaphis* 63-28 (formulated in coconut fiber and with 140 days' storage) or without infestation with the bacterial cells, and on the $2^{nd}$, $4^{th}$ and $6^{th}$ days after infestation of the nutrient solution with *P. chlororaphis* 63-28 (multiplied by 2 days and used without formulation) (FIG. 5). However, the values of the areas below the growth curves and the foliar growth rates were not significant by the test F (Table 1).

TABLE 1

Effect of infestation of the nutrient solution, or no infestation, of hydroponic lettuce with *Pseudomonas chlororaphis* 63-28, multiplied by two days or *Pseulomonas chlororaphis* 63-28 formulated in coconut fiber and stored for 140 days, on the $8^{th}$ day after infestation of the plants on the foliar growth area and the area of foliar growth rate.

| Treatments | Areas of foliar growth | Area of growth rate |
|---|---|---|
| Witness | 938.27* | 64.76 |
| *Pseudomonas chlororaphis* (2 days) | 976.73 | 71.82 |
| *Psudomonas chlororaphis* (140 days) | 967.95 | 72.21 |

*Data without letter were not significant by the F test.

Infestation of the nutrient solution with *P. chlororaphis* preserved in coconut fiber for 140 days promoted the development of the aerial system of hydroponic lettuce, statistically differing from the witness without inoculation (Table 2). The employ of bacterial cells cultured in TSB for two days promoted the development of the aerial system of the plants, but the difference was not statistically significant with respect to the witness treatment without infestation with the bacteria (Table 2). The mass data of the root system did not differ by the F test (Table 2).

TABLE 2

Effect of infestation, or absence of infestation, of the nutrient solution of hydroponic pimiento with *Pseudomonas chlororaphis* 63-28 cultured for two days or formulated in coconut fiber and preserved at 3 ± 1° C. for 140 days on the mass of hydroponic lettuce.

| Treatment | Fresh, of the aerial system (g) | Fresh, of the root system (g) | Fresh, total | Dry, of the aerial system (g) | Dry, of the root system (g) | Dray, total (g) |
|---|---|---|---|---|---|---|
| Witness | 88.65*b | 8.33* | 96.98 b | 5.02 b | 0.36 | 5.38 b |
| *Pseudomonas chlororaphis* (2 days) | 92.76 b | 8.47 | 101.23 b | 5.27 ab | 0.38 | 5.65 ab |
| *Psudomonas chlororaphis* (140 days) | 103.13 a | 8.69 | 111.82 a | 5.79 a | 0.39 | 6.18 a |

*data followed by the same letter were not significant in the LSD test, at 5%.
**Data without letter were no significant in the F test.

The invention claimed is:

1. A package comprising a formulation comprising effective amounts of:
    a) *Pseudomonas chlororaphis* and/or *Pseudomonas aureofaciens;*
    b) coconut fiber;
    c) water, in an amount such that said formulation has a moisture content of at least 45%;
    d) optionally, nutrient additives or growth factors selected from the group consisting of sugars, amino acids, proteins, salts and seeds, or mixtures thereof; and
    e) optionally, adjuvants selected from the group consisting of osmotic regulatory agents, buffering agents and pH adjusting agents.

2. The package according to claim 1, wherein said formulation further comprises a microorganism from a family, order or phylum selected from the group consisting of Actinobacteria, Aquificae, Bacteroidetes, Chlorobi, Chlamydiae, Verrucomicrobia, Chloroflexi, Chrisiogenetes, Cyanobacteria, Gloeobacteria, Nostocales, Oscillatoriales, Pleurocapsales, Prochlorales, Stigonematales, Deferribacteres, Deinococcus-Thermus, Dictyoglomi, Fibrobacteres, Acidobacteria, Firmicutes, Fusobacteria, Gemmatimonadetes, Nitrospirae, Planctomycetes, Proteobacteriz, Spirochaetes, Thermodesulfobacteria, and Thermotogae.

3. The package according to claim 1, wherein said formulation is formulated for the biological control of diseases and pests.

4. The package according to claim 3, wherein said pests are selected from the group consisting of caterpillars, cankerworms, acaridae, clothes moths, worms, beetles, cochineal insect, white flies, grass-hoppers, flea-insects, cochonilhas (*Coccus viridis*), centipedes, plant lice, spiders, ants, and insect larvae.

5. The package according to claim 3, wherein said diseases are caused by bacteria, fungi, zoopore producing pathogens, pathogens carried to the soil, root pathogens and pathogens of aerial parts of plants.

6. The package according to claim 5, wherein said pathogens carried to the soil are selected from a genus in the group consisting of *Pythium, Phytophthora, Fusarium,* and *Rhizoctonia.*

7. The package according to claim 1, wherein said formulation is able to promote plant growth.

8. The package according to claim 1, wherein said formulation is in a form selected from the group consisting of: a composition for suspension in water; a composition suspended in water; a dispersible formulation; grains; and a material for coating seeds and other propagation organs.

9. A method for the biological control of plant pathogens, comprising administering an effective amount of the formulation of the package according to claim 1 to seeds, seedlings, or a propagation material intended for plantation.

10. A method for the biological control of plant pathogens, comprising administering an effective amount of the formulation of the package according to claim 1 to a plant in need thereof in a culture substrate and/or in a nutrient solution.

11. A method for the biological control of plant pathogens, comprising administering an effective amount of the formulation of the package according to claim 1 to hydroponic cultures, substrates for producing seedlings, substrates for growing plants, or to soils.

12. A method for controlling a biological pest or disease, comprising administering an effective amount of the formulation of the package according to claim 1 to a plant in need thereof, or to seeds, seedlings, or a propagation material intended for plantation.

13. A method for promoting plant development, comprising administering an effective amount of the formulation of the package according to claim 1 to a plant in need thereof, or to seeds, seedlings, or a propagation material intended for plantation.

14. The package of claim 1, wherein said formulation contains between $1\times10^7$ to $1\times10^{11}$ colony forming units (cfu)/mL of said *Pseudomonas chlororaphis* and/or said *Pseudomonas aureofaciens.*

* * * * *